United States Patent [19]

Steiner et al.

[11] Patent Number: 5,126,078

[45] Date of Patent: Jun. 30, 1992

[54] AIR FRESHENER DISPENSER WITH REPLACEABLE CARTRIDGE EXHAUSTION ALARM

[75] Inventors: Robert L. Steiner, Chicago; Charles R. Holzner, both of Chicago; Kenneth D. Hartman, DeKalb; Donald B. Owen, Villa Park, all of Ill.

[73] Assignee: Steiner Company, Inc., Chicago, Ill.

[21] Appl. No.: 608,815

[22] Filed: Nov. 5, 1990

[51] Int. Cl.$^5$ ............................................... B01F 3/04
[52] U.S. Cl. ...................................... 261/26; 422/124; 340/636; 261/DIG. 65
[58] Field of Search ...................... 261/DIG. 65, 26; 422/124; 340/636

[56] References Cited

U.S. PATENT DOCUMENTS

| | | | |
|---|---|---|---|
| 2,614,820 | 10/1952 | Boydjieff | 261/26 |
| 3,522,481 | 8/1970 | Terzic | 340/636 |
| 3,990,848 | 11/1976 | Corris | 239/145 |
| 3,993,444 | 11/1976 | Brown | 261/DIG. 65 |
| 4,035,451 | 7/1977 | Tringali | 261/30 |
| 4,059,422 | 11/1977 | Steiner | 55/418 |
| 4,111,655 | 9/1978 | Quincey | 422/124 |
| 4,205,306 | 5/1980 | Turlej | 340/636 |
| 4,301,095 | 11/1981 | Mettler et al. | 261/30 |
| 4,383,951 | 5/1983 | Palson | 261/30 |
| 4,396,557 | 8/1983 | DeLuca | 261/30 |
| 4,695,435 | 9/1987 | Spector | 261/DIG. 65 |
| 4,743,406 | 5/1988 | Steiner et al. | 261/30 |
| 4,830,791 | 5/1989 | Muderlak et al. | 261/26 |
| 4,840,770 | 6/1989 | Walz et al. | 422/124 |
| 4,857,240 | 8/1989 | Keames et al. | 261/DIG. 65 |
| 4,931,224 | 6/1990 | Holzner, Sr. | 422/124 |
| 4,952,864 | 8/1990 | Pless et al. | 340/636 |

FOREIGN PATENT DOCUMENTS 2257134 5/1973 Fed. Rep. of Germany .

Primary Examiner—Tim Miles
Attorney, Agent, or Firm—Emrich & Dithmar

[57] ABSTRACT

An air freshener dispenser includes a two-part housing including a base and a separable cover. The base carries a control circuit and the cover carries a dispensing blower and a replaceable cartridge including the freshening agent to be dispensed and a battery for powering the blower. When the cover is removed from the base the blower is connected directly across the battery for test purposes, but when it is mounted on the base, contact structure on the cover and the base cooperate so that the blower is connected to the battery through the control circuit and is controlled thereby. The control circuit turns off the blower and triggers visible and audible alarm signals after a predetermined time period and/or when the battery voltage gets too low. A photocell turns off the blower and disables the audible alarm in the dark. The time-out period of the timer is selectively changeable.

19 Claims, 3 Drawing Sheets

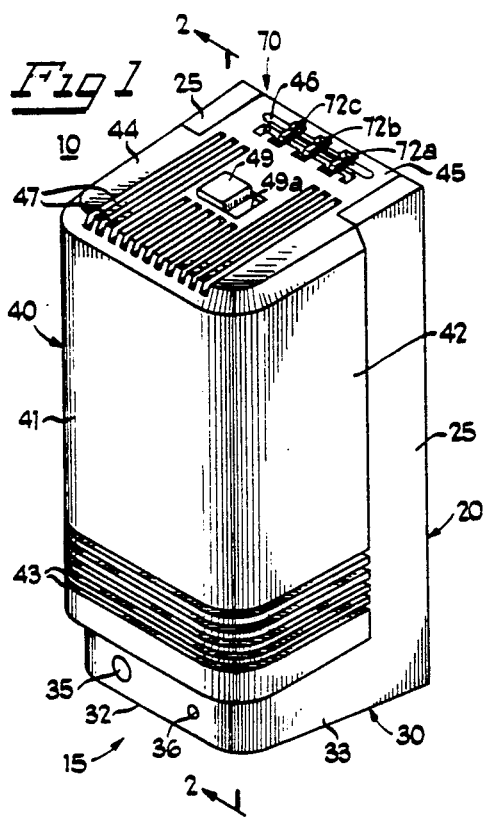
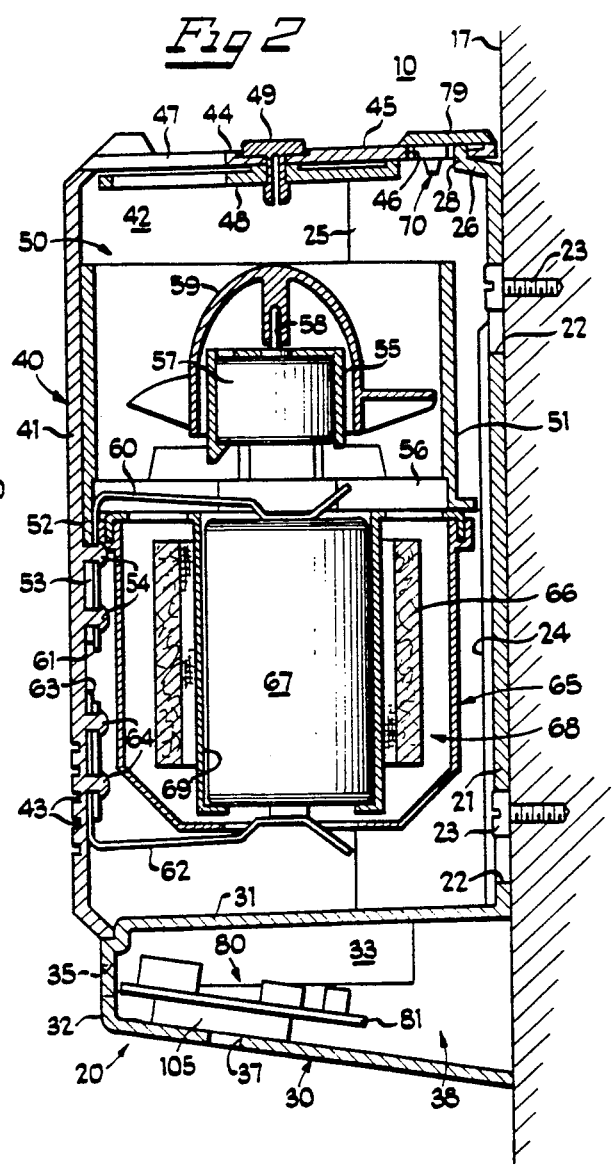
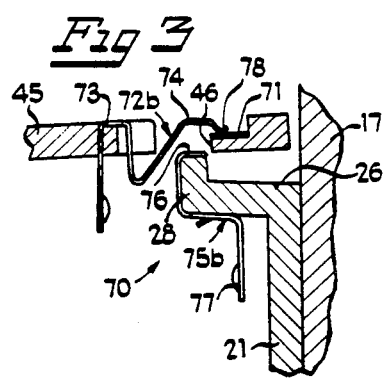
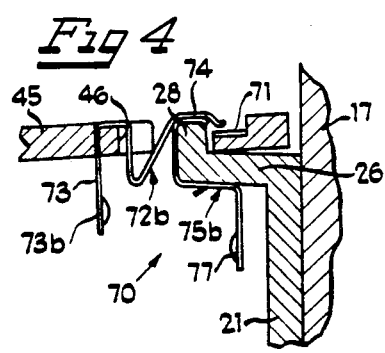
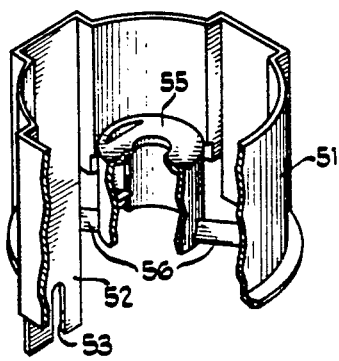

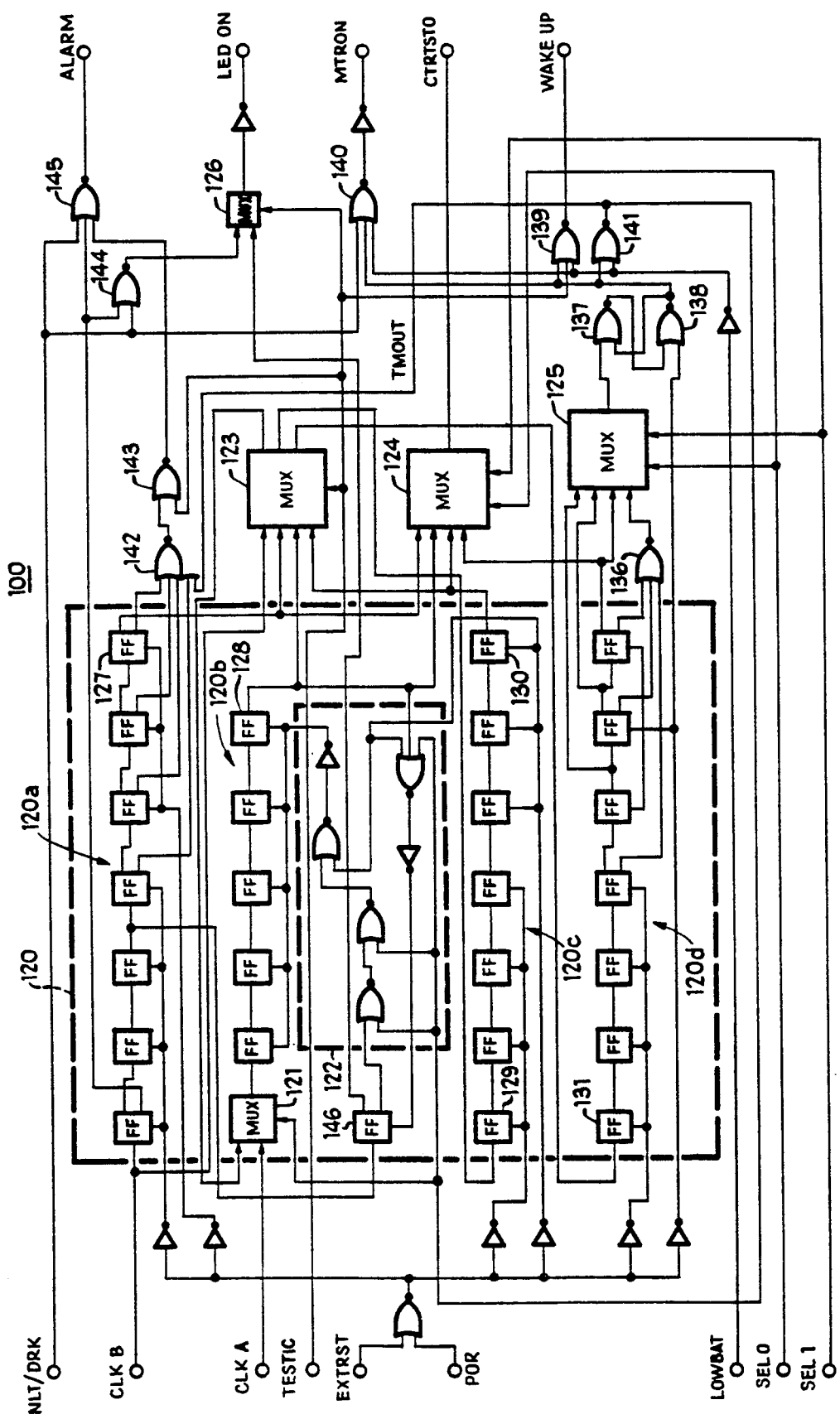

AIR FRESHENER DISPENSER WITH REPLACEABLE CARTRIDGE EXHAUSTION ALARM

BACKGROUND OF THE INVENTION

1. Field of the Invention

The present invention relates to dispensers, specifically air freshener dispensers. The invention has particular application to dispensers utilizing replaceable cartridges of the dispensed material.

2. Description of the Prior Art

There are many types of air freshener dispensers, including passive dispensers which simply provide apertures in a housing for exposing a supply of air freshening agent in the housing to the ambient air, and active dispensers which utilize some type of blower for positively dispensing the freshening agent into the ambient air. The latter type is commonly used in commercial applications. One type of active dispenser, disclosed, for example, in copending U.S. application Serial No. 445,273, has a replaceable cartridge which contains a supply of the air freshening agent and a battery-powered blower for dispensing the agent. A problem with such dispensers is that users seldom think to change the cartridges. It is not uncommon for a dispenser to remain empty for months before anyone puts in a new cartridge. In the meantime, the supply of air freshening agent will become exhausted and/or the battery will become discharged so that it can no longer power the blower.

In such prior active dispensers there is typically interconnection means on the replaceable cartridge and the support therefor which cooperate when the cartridge is mounted on the support for establishing an electrical circuit between the blower and the battery. Once the cartridge is mounted in place, however, the blower runs all the time, including night time and during weekends, holidays and other times when the premises may not be in use. This needlessly shortens the lifetime of both the battery and the supply of air freshening agent.

SUMMARY OF THE INVENTION

It is a general object of the present invention to provide an improved air freshener dispenser which avoids the disadvantages of prior dispensers while affording additional structural and operating advantages.

An important feature of the invention is the provision of an air freshener dispenser of the type using a replaceable cartridge with a battery-powered blower, which permits the operation of the battery and blower to be tested while the cartridge is separated from the support therefor.

Another feature of the invention is the provision of a battery-powered dispenser of the type set forth which conserves both battery power and the supply of air freshening agent.

In connection with the foregoing feature, it is another feature of the invention to provide a dispenser of the type set forth which automatically disables the dispenser blower during periods when it is not needed.

Still another feature of the invention is the provision of a replaceable cartridge dispenser of the type set forth which automatically provides a signal when a cartridge needs to be replaced.

In connection with the foregoing feature, another feature of the invention is the provision of a dispenser of the type set forth which automatically deactuates the blower when the cartridge replacement signal is active.

In connection with the foregoing features, a still further feature of the invention is the provision of a dispenser of the type set forth which generates an audible cartridge-replacement alarm signal which is automatically disabled at night.

These and other features of the invention are attained by providing in a dispenser having a housing with first and second separable portions, wherein the first portion includes a supply of a substance to be dispensed and a powered dispensing unit for the substance and an electric battery for powering the dispensing unit, the improvement comprising: control circuit means carried by the second housing portion, first coupling means on the first housing portion for directly connecting the dispensing unit across the battery when the first portion is separated from the second portion, and second coupling means on the second housing portion for cooperation with the first coupling means to connect the control circuit means to the dispensing unit and to the battery when the first portion is coupled to the second portion so that the dispensing unit operation is controlled by the control circuit means.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a front perspective view of a dispenser constructed in accordance with and embodying the features of the present invention, including a housing having a cover removably mounted on a support;

FIG. 2 is a view in vertical section taken along the line 2—2 in FIG. 1 and including a contact cover over the contact assembly;

FIG. 3 is an enlarged fragmentary view of the electrically interconnectable portions of the cover and the support when the cover is demounted from a support;

FIG. 4 is a view similar to FIG. 3, illustrating the interconnection between the cover and the support in their mounted condition;

FIG. 5 is a fragmentary perspective view of the blower shroud of the dispenser of FIG. 2;

FIG. 7 is a logic circuit diagram of the logic block of the ASIC of FIG. 6.

DESCRIPTION OF THE PREFERRED EMBODIMENT

Figure 6:
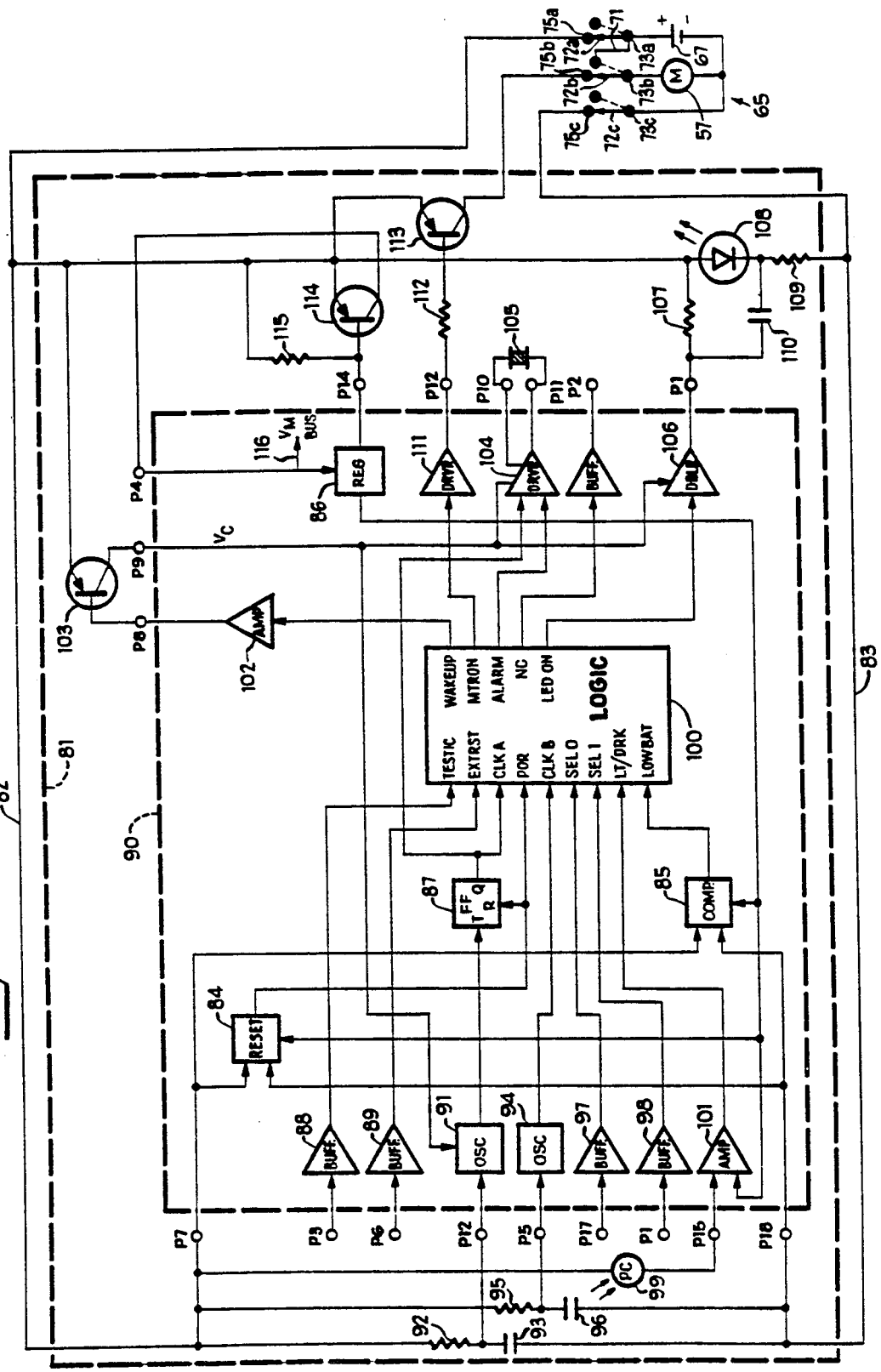
FIG. 6 is a partially block and partially schematic circuit diagram of the control circuitry for the dispenser of FIG. 1.

Referring to FIGS. 1 and 2, there is illustrated an air freshener dispenser 10, constructed in accordance with and embodying the features of the present invention. The dispenser 10 includes a two-part housing 15 having a support base 20 and a removable cover 40, and adapted to be mounted on an associated support surface, such as a wall 17. The support base 20 includes an upstanding generally rectangular back panel 21 having openings 22 therein for receiving fasteners 23 securely to attach the panel 21 to the wall 17. The panel 21 has a forwardly projecting hollow rib 24 therein (FIG. 2) extending vertically substantially the length thereof and defining a wiring channel. Integral with the back panel 21 along the opposite side edges thereof and projecting forwardly therefrom are a pair of generally rectangular side flanges 25. Projecting forwardly from the upper edge of the back panel 21 is a short top flange 26 provided at its distal end with an upstanding lip 28.

Projecting forwardly from the lower end of the back panel 21 is a pedestal 30 which includes a top wall 31 which is integral with the lower edge of the back panel 21. Depending from the front end of the top wall 31 is a front wall 32 which, in turn, is integral at its lower edge with a downwardly and rearwardly projecting bottom wall 34. The pedestal is closed by a pair of side walls 33. Formed in the front wall 32 are openings 35 and 36, and an opening 37 is formed in the bottom wall 34. Thus, it will be appreciated that the walls of the pedestal 30 cooperate to define a compartment or chamber 38 which opens to the rear.

The cover 40 includes a rectangular front wall 41 integral at its side edges with rearwardly projecting side walls 42. Vent openings 43 extend laterally along the entire width of the front wall 41 and the side walls 42. Integral with the front wall 41 and the side walls 42 at the upper edges thereof is a top wall 44 provided at its rearward edge with a rearwardly projecting flange 45 having an irregular slot 46 formed therein and extending laterally thereof. Also formed in the top wall 44 are vent openings 47. A slider plate 48 is disposed along the inner surface of the top wall 44 and is secured to a knob 49 which projects upwardly through a complementary slot opening 49a in the top wall 44 for effecting sliding movement of the slider plate 48 to control the opening of the vent openings 47.

Mounted in the cover 40 is a blower assembly 50, which may be of a type disclosed in the aforementioned U.S. application Ser. No. 445,273, and includes a generally cylindrical shroud 51 having a mounting flange 52 depending therefrom. A vertical slot 53 in the lower edge of the mounting flange 52 is adapted to be received over a pair of vertically aligned lugs 54 projecting rearwardly from the front wall of the cover 40 for securing the shroud 51 in place. The shroud 51 is open at its upper end. Disposed coaxially withing the shroud 51 is a turret 55 generally in the shape of an inverted cylindrical cup, the lower end of which is connected to the shroud 51 by a plurality of circumferentially spaced-apart and radially extending webs 56. A DC motor 57 is mounted in the turret 55 and has an output shaft 58 which projects upwardly through a complementary opening in the upper wall of the turret 55 and is there attached to the hub of a turbo fan 59 for rotation by the motor 57.

A resilient, flexible, electrically conductive battery contact 60 is disposed immediately beneath the shroud 51 and is provided with a depending mounting arm 61 which is fixedly secured to the lugs 54. A lower resilient metallic battery contact 62 is disposed adjacent to the lower end of the cover 40 and is provided with an upstanding mounting arm 63 which is fixedly secured to a pair of vertically spaced-apart lugs 64 projecting rearwardly from the front wall 41 of the cover 40.

A generally cylindrical replaceable cartridge 65 is removably mountable on the cover 40. The cartridge 65 defines an annular chamber 68 in which is disposed an annular medium 66 containing a supply of air freshening agent, which may be a volatile substance of any desired fragrance. For example, the medium 66 may be in the nature of a felt cylindrical body impregnated with the air freshening agent. The cartridge 65 also contains an inner axial chamber 69 in which is disposed a battery 67 which may be a 1.5 volt cell. The annular chamber 68 is provided with openings at the upper and lower ends thereof to accommodate free flow of air therethrough, and the axial chamber 69 is open at its upper and lower ends to permit the battery contacts 60 and 62 to resiliently engage the negative and positive terminals of the battery 67 for electrical contact therewith, when the cartridge 65 is inserted between the contacts 60 and 62, which also serve resiliently to retain the cartridge 65 in place. If desired, the cartridge 65 may be provided with anti-bootleg apparatus (not shown) of the type disclosed in U.S. Pat. No. 4,931,224.

Referring also to FIGS. 3 and 4, the housing 15 includes an electrical contact assembly 70 which includes contacts on the flange 45 of the cover 40 and contacts on the lip 28 of the support base 20 for cooperation with each other when the cover 40 is mounted on the support base 20 for connecting the battery 67 and the motor 57 to a control circuit 80, as will be explained more fully below in connection with FIG. 7. The contact assembly 70 includes three sets of contacts, schematically illustrated in FIG. 6 with the mechanical details of one of the sets being illustrated in FIGS. 3 and 4. The sets are respectively labeled with suffixes "a", "b" and "c". For purposes of illustration, the set "b" is illustrated in FIGS. 3 and 4.

The set "b" of the contact assembly 70 includes a fixed contact 71 on the flange 45 at one side of the slot 46, the contact 71 being connected to the battery contact 62 which is, in turn, adapted to be connected to the positive terminal of the battery 67. There is also provided a movable contact 72b which includes a mounting portion 73 fixedly secured to the flange 45 at the other side of the slot 46 and a movable leaf spring 74 which extends across the slot 46 and terminates in a tip 78 which is normally resiliently urged into engagement with the fixed contact 71. The mounting portion 73 is provided with a connection tab 73b which is, in turn, connected to one terminal of the motor 57. There is also provided a fixed contact 75b mounted on the lip 28 of the support base 20 and having a bearing portion 76 which is wrapped around the top of the lip 28 and a connection tab 77 which is connected to the control circuit 80, as will be explained below.

As can be seen in FIGS. 3 and 4, when the cover 40 is removed from the support base 20, the movable contact 72b is disposed in electrical contact with the fixed contact 71 for directly connecting the motor 57 across the battery 67. When the cover 40 is mounted on the support base 20, the lip 28 fits into the slot 46, with the bearing portion 76 of the fixed contact 75b engaging the leaf spring 74 of the movable contact 72b for establishing electrical connection therebetween and for moving the movable contact 72b out of contact with the fixed contact 71. Thus, when the cover 40 is mounted on the support base 20, the motor 57 is connected to the battery 67 through the control circuit 80.

The "a" and "c" sets of the contact assembly 70 are substantially identical to the "b" set illustrated in FIGS.

3 and 4, except that they do not include the fixed contact 71. Thus, the "a" and "c" sets essentially operate as single-throw switches, while lthe "b" set operates as a double-throw switch. If desired, a contact cover 79 may be disposed over the slot 46 for covering the contact assembly 70 when the cover 40 is mounted on the support base 20 (see FIGS. 1 and 2).

Referring now to FIG. 6, there is illustrated a control circuit 80 for controlling the operation of the dispenser 10. The control circuit 80 includes a printed circuit board 81 which is disposed in the chamber 38 of the pedestal 30 (see FIG. 2), and is connected by suitable conductors to the fixed contacts 75a–c of the contact assembly 70 which are mounted on the support base 20. More specifically, a conductor 82 is connected to the fixed contact 75a which is, in turn, connectable to the positive terminal of the battery 67 through the "a" contact set when the cover 40 is mounted in place on the support base 20. A conductor 83 is connected to the fixed contact 75c which is, in turn, connectable to the negative terminal of the battery 67 and to one terminal of the motor 57 through the "c" contact set when the cover 40 is mounted in place one the support base 20.

The control circuit 80 includes an application specific integrated circuit ("ASIC") 90 which has a logic unit 100. The ASIC 90 has terminal pin P1–P18 which are connectable to discrete circuit components mounted on the PC board 81. The ASIC 90 includes a power-on reset circuit 84 and a low voltage detection comparator 85 which are connected in parallel across the power and ground terminals P7 and P18 of the ASIC 90, which terminals are, in turn, respectively connected by the conductors 82 and 83 to the terminals of the battery 67. When the battery voltage is below a reference voltage level provided by a regulator circuit 86, the comparator 85 applies a logic level to a low battery (LOWBAT) input terminal of the logic unit 100 for controlling motor control and alarm control circuitry therein, as will be explained more fully below. When the battery output voltage level is above the predetermined reference level (e.g., 1.2 volts), it is recognized as a good battery and, therefore, upon connection of the ASIC 90 to this battery voltage, the output signal from the reset circuit 84 is applied to the POR input terminal of the logic unit 100 to reset all of the circuit elements in the logic unit 100. If the battery output voltage is below the reference level, it will be too low to reliably operate the dispenser 10 and, accordingly, the output signal from the comparator 85 supplies a logic level to motor control and alarm control circuits in the logic unit 100 to disable the fan motor 57 and enable alarm condition signals, as will be described more fully below.

The output of the comparator 84 is also applied to a reset terminal of a flip-flop 87. Buffer amplifiers 88 and 89, respectively, have inputs connected to the terminals P3 and P6 of the ASIC 90, and have outputs respectively connected to an IC test (TESTIC) terminal and an external reset (EXTRST) terminal of the logic unit 100. The terminals P3 and P6 of the ASIC 90 are not connected in normal use, but are usable for connecting test procedures for the ASIC 90.

The ASIC 90 further includes an oscillator 91, which supplies an audio signal for a piezo driver circuit and a short (5 ms.) pulse for an LED flasher circuit, as will be explained more fully below. The oscillator 91 is powered by a voltage level $V_c$ and has an input connected to the terminal P12 of the ASIC 90 which is, in turn, connected to the junction between a resistor 92 and a capacitor 93 which are connected in series across the battery terminal conductors 82 and 83. The oscillator 91 generates a variable periodic signal at a frequency (e.g., 3.3 KHz) determined by the resistor 92 and capacitor 93 and applies it to the T input terminal of the flip-flop 87, the Q output of which is applied to a CLKA input terminal of the logic unit 100. The ASIC 90 also includes an oscillator 94 which provides a constant frequency signal for use as a timing or audio signal in the logic unit 100, as will be explained more fully below. The oscillator 94 has an input connected to the terminal P5 which is, in turn, connected to the junction between a resistor 95 and a capacitor 96 which are connected in series across the battery terminal conductors 82 and 83, these elements controlling the frequency of the output signal of the oscillator 94, which is applied to a CLKB input terminal of the logic unit 100. The constant frequency output signal of the oscillator 94 is created through a charge/discharge cycle of the capacitor 96, which is allowed to charge through the resistor 95 to about 5/6 of the battery voltage and is then quickly discharged through a transistor (not shown) in the oscillator 94.

The ASIC 90 includes input buffer amplifiers 97 and 98, the inputs of which are respectively connected to the terminals P17 and P1 of the ASIC 90 and the outputs of which are respectively connected to SEL0 and SEL1 input terminals of the logic unit 100. The logic unit 100 includes a timing circuit which has a countdown period length which is selectable by logic levels set on the terminals P17 and P1 by appropriate external connections (not shown). This provides a two-digit binary input code which permits selection among four different time-out periods. It will be appreciated that the input buffer circuits 88, 89, 97 and 98 electrically isolate the external control signals from the internal logic current paths and transform the external logic signal levels to levels and impedances corresponding to the internal logic circuitry of the logic unit 100.

The control circuit 80 also includes a photoresistor 99, which may be a cadmium sulfide cell which is connected between the positive battery terminal conductor 82 and the terminal P15 of the ASIC 90, the latter in turn being connected to one input terminal of a photo amplifier 101 of the ASIC 90, the other input of which is connected to the reference voltage level. The reference voltage level corresponds to a predetermined light level (e.g., 0.5 foot-candles), and when the photoresistor 99 senses that the ambient light level has dropped below this reference level, the photo amplifier 101 outputs a signal to the NLT/DRK input terminal of the logic unit 100 for disabling the blower motor 57, in a manner to be described below. The photo amplifier 101 serves to transform the light-dependent resistance of the photoresistor 99 into a logic level signal for use in the motor control circuitry of the logic unit 100.

When the internal timer of the logic unit 100 times out, it outputs a signal at the WAKEUP terminal which is applied through an output buffer amplifier 102 to the terminal P8 of the ASIC 90 which is, in turn, connected to the base of a transistor 103, the emitter of which is connected to the positive battery terminal conductor 82, and the collector of which is connected to the terminal P9 of the ASIC 90. The transistor 103 provides the $V_c$ voltage level to the terminal P9, which is connected not only to the oscillator 91, but also to a driver circuit 104, which also has inputs respectively connected to the Q output of the flip-flop 87 and to an ALARM output terminal of the logic unit 100. Since the $V_C$ voltage level is provided in response to the time-out of the timer, the oscillator 91 is idle during countdown of the timer.

In operation, when the $V_C$ voltage level is present, the oscillator 91 generates an audio output signal which is applied through the flip-flop 87 to the driver 104 which, in the presence of the ALARM output signal from the logic unit 100, generates an low-impedance, bipolar drive signal which is connected across the terminals P10 and P11 of the ASIC 90 for driving a piezoelectric audio resonator 105 which is also connected across the terminals P10 and P11. The driver circuit 104 serves to transform the internal impedance and voltage levels of the audio alarm signal from the oscillator 91 to a level sufficient to directly drive the resonator 105.

The $V_C'$ voltage level is also applied to a voltage doubler circuit 106, which also receives an input from an LEDON output terminal of the logic unit 100. The output of the voltage doubler circuit 106 is connected to the terminal P1 of the ASIC 90, which is in turn connected through a resistor 107 to the anode of an LED 108, which is also connected to the positive battery terminal conductor 82. The cathode of the LED 108 is connected through a resistor 109 to the negative battery terminal conductor 83 and, through a capacitor 110, to the ASIC terminal P1. In use, the voltage doubler circuit 106 serves to periodically flash the LED 108 after the end of the timer countdown or when the battery voltage falls below a predetermined level. Thus, in the presence of the voltage level $V_C$ the voltage doubler circuit 106 serves to discharge the capacitor 110 in a transient periodic fashion, controlled by a strobe signal from the LEDON terminal of the logic unit 100. Each discharge of the capacitor 110 causes its voltage to appear in series with the battery voltage through the resistor 107, thereby turning on the LED 108 to generate a burst of light. The ASIC terminal P2 is not connected.

The logic unit 100 has an MTRON output terminal which is connected to the input of an open collector fan driver circuit 111, the output of which is connected to the terminal P12 of the ASIC 90. The terminal P12 is connected through a resistor 112 to the base of a transistor 113, the collector of which is connected to the contact 75b of the contact assembly 70 for connection to the other terminal of the blower motor 57. The emitter of the transistor 113 is connected to the positive battery terminal conductor 82 and to the emitter of a transistor 114, the base and the collector of which are, respectively, connected to the terminals P14 and P4 of the ASIC 90. A resistor 115 is connected across the base-emitter junction of the transistor 114. The MTRON signal from the logic unit 100 is applied to the driver circuit 111, which provides a low-impedance drive signal to turn on the transistor 113, thereby turning on the blower motor 57 by connecting it across the battery terminals.

There are two supply voltage buses (not shown) supplying different supply voltage levels to the logic and other circuit elements of the ASIC 90, viz., the battery voltage which appears across terminals P7 and P18 and a voltage level $V_M$ which is present at the terminal P4 and is connected via a conductor 116 to the $V_M$ bus. This voltage level is also applied to the regulator circuit 86, which has an output connected to the terminal P14 of the ASIC 90. The regulator circuit 86 serves to stabilize the voltage level $V_M$ over the life of the battery 67. It essentially compares the voltage level $V_M$ to the battery voltage and, as the battery voltage decreases, the regulator circuit 86 changes the bias on the transistor 114 to maintain the voltage level $V_M$ and thereby provide constant current operation for the logic circuitry.

Referring to FIG. 7, there is illustrated a logic diagram of the elements of the logic unit 100. The logic unit 100 includes a timer section 120 which is a cascade network of 26 flip-flop dividers, a multiplex circuit 121 and a gate array 122. The logic unit 100 also includes multiplex circuits 123–126 along with associated gates and buffers. The cascade network is subdivided into four serially connected chains 120a, 120b, 120c and 120d.

The logic unit 100 has two operational modes, viz., a countdown mode and an alarm mode. The countdown mode is initiated by the power-on reset sequence. Thus, when the battery is connected to the control circuit 80, if it is a good battery the output of the reset circuit 84 at terminal POR resets all of the flip-flops in the logic unit 100. The clock signal CLKB from the oscillator 94 is applied to the beginning of the first divider chain 120a of the timer section 120 and is also applied to the multiplex circuit 123. The timer section 120 can count down to any one of four different countdown intervals, as selected by the logic inputs SEL0 and SEL1, which are applied to the multiplex circuits 124 and 125.

The output of the seventh divider 127 of the first divider chain 120a is applied through the multiplex circuit 123, being passed from the C1 output thereof through the multiplex circuit 121 to the first divider of the next divider chain 120b. Similarly, the output of the last divider flip-flop 128 of the divider chain 120b is passed through the multiplex circuit 123 and via its output C2 to the first divider 129 of the divider chain 120c. Then the output of the last divider 130 in the divider chain 120c is passed through the multiplex circuit 123 and via its output C3 to the first divider 131 in the last divider chain 120d. The Q outputs of the last three dividers in the divider chain 120d are, respectively, connected to three of the inputs of the multiplex circuit 125, while the $-Q$ outputs of the last divider, the second to the last divider and the fourth to the last divider in the chain are connected through the NOR gate 136 to the fourth input terminal of the multiplex circuit 125. The available number of time periods is $2^{23}$, $2^{24}$, $2^{25}$, and $2^{22}+2^{24}+2^{25}$. These divide sequences correspond, respectively, to 14, 28, 56 and 91 days for a nominal 6.93 Hz. clock input signal. During countdown, the timer section 120 will continue to operate unless its operating mode is modified by an input at the external reset (EXTRST) terminal, the IC test (TESTIC) terminal or the low battery detections (LOWBAT) terminal.

The multiplex circuit 125 will generate an output alarm signal at the time-out of the selected time interval, which output is buffered through NOR gates 137 and 138 to provide a signal which is, in turn, fed through a NOR gate 139 to provide the WAKEUP output signal. The selected time-out interval is the life expectancy of the air freshening agent supply and/or the battery in the cartridge 65. In this normal countdown mode of operation, the MTRON output signal is generated by combining the NLT/DRK input signal with the inverted LOWBAT input signal and with the output of the gate 138 in the NOR gate 140. Thus, if the ambient light level is above 0.5-foot candles, and the battery voltage is above 1.2 VDC and the timing interval has not expired, the blower motor 57 will be on. This is the ordinary operating mode for the circuit. The MTRON drive signal will be removed if the ambient light level drops below 0.5-foot candles or if the battery voltage drops below 1.2 VDC, or if the selected timing interval expires.

When this interval expires, the output of the gate 138 is also combined with the inverted LOWBAT signal in a NOR gate 141 to provide a TMOUT signal which is combined with outputs from the last four dividers of the divider chain 120a in a NOR gate 142, the output of which is fed through NOR gates 143 and 145 to generate the ALARM signal to enable the driver circuit 104. The presence of the WAKEUP signal turns on the transistor 103 to apply the $V_C$ voltage level to power the driver 104 (see FIG. 6). The TMOUT signal is also applied to the multiplex circuit 121 for passing the CLKA oscillator signal to the divider chain 120b, the output of which is applied to the gate array 122 which also receives the TMOUT signal to apply a strobe signal to the multiplex circuit 126, which generates the LEDON signal for strobing the LED 108 through the voltage doubler circuit 106.

The output of the first divider in the divider chain 120a, which has a frequency of about 4 Hz, is applied to the NOR gates 144 and 145, each of which also receives the NLT/DRK signal. The output of the gate 144 is also applied to the multiplex circuit 126 for strobing the LEDON signal on about 4 times per second, the output of a flip-flop 146 also being applied to the multiplex circuit for turning the LEDON signal off. The flip-flop 146 is triggered by the output of the third divider in the divider chain 120a so that each LEDON pulse lasts about 5 ms.

The multiplex circuit 123 is used in the IC test mode to generate audio signals at a predetermined rate for test purposes.

In operation, when it is desired to install a cartridge 65 in the dispenser 10, the cover 40 is removed from the support base 20 and the cartridge 65 is inserted in the cover 40 between the battery contacts 60 and 62, as illustrated in FIG. 2. This connects the battery 67 across the terminals of the blower motor 57, as indicated by the broken line contact positions in FIG. 6. If the battery 67 is good, the blower assembly 50 will begin to operate, serving as a quick test for the battery. It will be appreciated that the circuit board 81 is so positioned in the chamber 38 of the pedestal 30 that the LED 108 is aligned with the opening 35 in the pedestal front wall 32, the photocell 99 is aligned with the opening 36 in the front wall 32 (see FIG. 1), and the piezoelectric resonator 105 is aligned with the opening 37 in the bottom wall 34.

The cover 40 is then mounted on the support base 20, as illustrated in FIGS. 2 and 4, thereby interconnecting the sets 72a-c and 75a-c of the contact assembly 70, for breaking the connection between the motor 57 and the battery 67 and connecting the circuit board 81 in circuit between the battery 67 and the motor 57, as illustrated by the solid-line contact positions in FIG. 6. This will place the motor 57 under the control of the control circuit 80. Assuming that the battery 67 is good, its connection to the circuit board 81 will cause a reset signal to be output from the reset circuit 84 to the POR input of the logic unit 100, resetting the timer section 120 (FIG. 7), which will then immediately start to divide the oscillator input signal being fed to the CLKB input and count down the timer interval period, which is preferably preset at the factory by appropriate selection of the SEL0 and SEL1 inputs to the logic unit 100. If the ambient light level is above 0.5-foot candles, the MTRON output signal will be generated and turn on the blower motor 57 in the manner described above, and the dispenser 10 will begin operation in its normal mode. In this regard, it will be appreciated that the blower fan 59 will draw air in the vent openings 43, through the cartridge 65 and over the freshening agent medium 66 and then out through the vent openings 47 and into the ambient air for dispensing the air freshening agent. It will be appreciated that the vent openings 47 can be adjusted by means of the slider plate 48.

This normal operation will continue until the ambient light level drops below 0.5 foot candles, which will typically occur at night, or on weekends, holidays or other periods of nonuse, when either sunlight is unavailable or artificial lights have been extinguished. Since, at such times there is no need for the dispensing of the air freshening agent, the amplifier 101 inputs a signal to the NLT/DRK input of the logic unit 100 (FIG. 6), which is applied through the gate 140 to terminate the MTRON signal and deenergize the blower motor 57. This stops the flow of air over the medium 66, thereby slowing down the evaporation of the air freshening agent and conserving its supply. Also, the shut off of the blower motor 57 conserves battery energy and prolongs the life of the battery 67. When the ambient light level goes back above 0.5-foot candles, the blower motor 57 is turned back on. It will be appreciated from FIG. 7 that when the NLT/DRK signal is applied to the logic unit 100, it will also generate the ALARM output signal, which is applied to the driver 104. However, no audible alarm is generated, because the driver circuit 104 is not powered, since the transistor 103 is turned off. Similarly, the LEDON signal will be generated, but it has no effect since the voltage doubler 106 is not powered.

When the selected timer interval expires, the multiplex circuit 125 will generate an output signal which is applied through the gates 137-139 to provide the WAKEUP signal, which turns on the transistor 103, thereby applying the $V_c$ voltage to the ASIC 90. This voltage turns on the oscillator 91, causing it to output an audio signal through the flip-flop 87 to the CLKA input terminal of the logic unit 100 and to the driver 104. The $V_c$ voltage level is also applied directly to the driver 104 and to the voltage doubler circuit 106 for powering them. The interval time-out signal TMOUT is also applied through the gates 142, 143 and 145 to produce the ALARM signal which is applied to the driver 104 and triggers it to pass the oscillator signal from the flip-flop 87 for resonating the piezoelectric driver 105 to produce an audible alarm signal. An output from the first divider in the divider chain 120a renders the audible alarm signal intermittent, i.e., the piezoelectric element 105 is strobed on approximately 4 times per second in a short burst which is repeated once every 16 seconds. The 16-second interval is controlled by the output from the divider 127 applied through the gate 142. The output of the gate 144 also triggers the LEDON signal and, since the voltage doubler circuit 106 is now powered, the LED 108 is strobed by the LEDON signal to generate a visible alarm signal. The audio and LED signals will continue until there is no longer sufficient energy in the battery 67 to drive the circuitry. The audible and visible alarms signal the users that it is time to replenish the supply of air freshening agent in the cartridge 65.

When the battery voltage drops below about 1.2 volts, whether or not the timer section 120 has timed out, the application of the inverted LOWBAT signal to the gate 140 will remove the MTRON signal, turning off the blower motor 57. This inverted LOWBAT signal is also applied to the gates 139 and 141 to generate the WAKEUP alarm signal and to generate the TMOUT signal for triggering the LED and audible alarms, just as was explained above in the case of time-out of the timer. Thus, the user will be warned that the battery needs replacement.

Since the same alarm signals are given in either alarm condition, the user does not know whether the alarm signal is caused by time-out of the timer section 120 or by a low battery condition. But he need not know since, preferably, the air freshening agent supply will be arranged to have generally the same life expectancy as the battery. Thus, when an alarm condition sounds, the user simply replaces the entire cartridge 65, supplying a fresh battery and a fresh supply of air freshening agent.

It is a significant aspect of the present invention that the design of the control circuit 80 is such that it consumes very little power. Thus, even after the battery voltage has dropped below 1.2 volts, the alarm signals will continue to be generated for about four days, where the battery 67 is a standard 1.5 volt "D" cell. Furthermore, the control circuit 80 is so arranged that, while a "worn-out" battery may have sufficient energy to continue to operate the alarm signals, once its output voltage has dropped below 1.2 volts it will not be capable of resetting and restarting the timing circuitry. Rather, this circuitry cannot be reset unless a good battery with sufficient voltage is installed.

From the foregoing, it can be seen that there has been provided an improved air freshener dispenser which is of simple and economical construction and which provides a positive test of battery condition and which clearly alerts the user to the need for replacement of either the blower battery or the supply of air freshening agent.

We claim:

1. In a dispenser having a housing including first and second separable portions, wherein the first portion includes a supply of a substance to be dispensed and a powered dispensing unit for the substance and an electric battery for powering the dispensing unit, the improvement comprising: control circuit means carried by the second housing portion, first coupling means on the first housing portion for directly connecting the dispensing unit across the battery when the first housing portion is separated from the second housing portion, and second coupling means on the second housing portion for cooperation with said first coupling means to connect said control circuit means to the dispensing unit and to the battery when the first housing portion is coupled to the second housing portion so that the dispensing unit operation is controlled by said control circuit means.

2. The dispenser of claim 1, wherein the substance to be dispensed is an air freshening agent.

3. The dispenser of claim 1, wherein said first and second coupling means include electrical contact means.

4. The dispenser of claim 3, wherein said first coupling means includes a first fixed contact connected to the battery and a movable contact connected to the dispensing unit and movable between a normal first position biased into electrical connection with said first fixed contact and an open position spaced from said first fixed contact, said second coupling means including a second fixed contact engageable with said movable contact for electrical connection therewith and for movement thereof to the second position thereof.

5. The dispensing apparatus of claim 1, wherein said control circuit means includes alarm means for generating an alarm signal in response to the occurrence of a predetermined alarm condition.

6. The dispenser of claim 5, wherein said alarm means includes timing means responsive to coupling of the first housing portion to the second housing portion for generating an alarm signal a predetermined time period thereafter.

7. The dispenser of claim 6, wherein said alarm means includes voltage sensing means coupled to the battery and to said timing means for preventing actuation of said timing means to initiate said predetermined time period if the battery output voltage is below a predetermined voltage level when the first housing portion is coupled to the second housing portion.

8. The dispenser of claim 5, wherein said alarm means includes voltage sensing means coupled to the battery and responsive to the output voltage thereof for producing an alarm signal when the battery output voltage drops below a predetermined voltage level.

9. The dispenser of claim 1, wherein said control circuit means includes photoelectric means responsive to the absence of a predetermined level of ambient light for altering the performance of said control circuit means.

10. The dispenser of claim 9, wherein said control circuit means includes means coupled to said photoelectric means and cooperating therewith to deenergize the dispensing unit in the absence of the predetermined level of ambient light.

11. An air freshener dispenser comprising: a supply of an air freshening agent, a blower for dispensing the air freshening agent into the ambient air, a battery for providing power to operate said blower, and timing means adapted for connection to said battery and responsive to such connection for generating an alarm signal a predetermined time period after such connection, said timing means including means for generating an audible alarm signal, and photoelectric means for disabling the audible alarm signal in the absence of a predetermined level of ambient light.

12. The dispenser of claim 11, wherein said timing means includes means for selectively changing said predetermined time period.

13. The dispenser of claim 11, wherein said timing means includes means for generating a visible alarm signal.

14. A dispenser comprising: a supply of a substance to be dispensed, separable housing means containing a powered dispensing unit for the substance, an electric battery for powering the dispensing unit, control circuit means, and switch means switchable between first and second conditions in response to separation of said housing means, said switch means in the first condition thereof disconnecting said battery from said control means and directly connecting said dispensing unit across said battery, said switch means in the second condition thereof connecting said dispensing unit to said battery through said control circuit means so that the operation of said dispensing unit is controlled by said control circuit means.

15. An air freshener dispenser comprising: a housing, a supply of an air freshening agent disposed in said housing, a blower disposed in said housing for dispensing the air freshening agent into the ambient air, a battery disposed in said housing and connected to said blower for supplying DC power thereto for operation thereof, alarm means for generating an alarm signal, timing means coupled to said alarm means and adapted for connection to said battery and responsive to such connection for actuating said alarm means a predetermined time period after such connection, and low voltage detection means disposed in said housing and coupled to said alarm means and to said battery and responsive to the output voltage of said battery for actuating said alarm means when the battery output voltage drops below a predetermined voltage level.

16. The dispenser of claim 15, wherein said alarm means includes means for generating a visible alarm signal.

17. The dispenser of claim 15, wherein said alarm means includes means for deactuating said blower when the battery output voltage drops below the predetermined voltage.

18. The dispenser of claim 15, wherein said alarm means includes means for generating an audible alarm signal.

19. The dispenser of claim 18, wherein said alarm means includes photoelectric means for disabling the audible alarm signal in the absence of a predetermined level of ambient light.

* * * * *